(12) United States Patent
Hayashi et al.

(10) Patent No.: US 6,406,147 B1
(45) Date of Patent: Jun. 18, 2002

(54) VISUAL ACUITY TESTING APPARATUS

(75) Inventors: Akihiro Hayashi, Toyokawa; Yuichiro Kanazawa, Okazaki; Noritsugu Nozawa, Toyokawa, all of (JP)

(73) Assignee: Nidek Co., Ltd., Aichi (JP)

( * ) Notice: Subject to any disclaimer, the term of this patent is extended or adjusted under 35 U.S.C. 154(b) by 121 days.

(21) Appl. No.: 09/612,593

(22) Filed: Jul. 7, 2000

(30) Foreign Application Priority Data

Jul. 9, 1999 (JP) .......................................... 11-196680
Jul. 9, 1999 (JP) .......................................... 11-196681

(51) Int. Cl.⁷ ................................................ A61B 3/02
(52) U.S. Cl. ..................................................... 351/239
(58) Field of Search ................................ 351/220, 221, 351/232, 237, 239, 240, 243, 244, 245

(56) References Cited

U.S. PATENT DOCUMENTS 4,274,715 A * 6/1981 Reiner ........................ 351/237
5,629,748 A * 5/1997 Hayashi et al. ............. 351/232
5,870,168 A * 2/1999 Kirchhuebel et al. ....... 351/221
6,139,151 A * 10/2000 Ueno et al. ................. 351/220

FOREIGN PATENT DOCUMENTS

JP          2754034       4/1989
JP          2000-126131   5/2000

* cited by examiner

*Primary Examiner*—George Manuel
(74) *Attorney, Agent, or Firm*—Finnegan, Henderson, Farabow, Garrett & Dunner, L.L.P.

(57) ABSTRACT

A visual acuity testing apparatus comprises a casing having at least one test window which an examinee looks into, and at least one optotype presented inside the casing which is disposed in such a position that its optotype plane is tilted relative to a datum plane orthogonal to an axial line connecting the test window to an optotype presentation position in order to prevent that light entered through the test window and reflected from the optotype plane, passes through he test window again.

17 Claims, 6 Drawing Sheets

VISUAL ACUITY TESTING APPARATUS

BACKGROUND OF THE INVENTION

1. Field of the Invention

The present invention relates to a visual acuity testing apparatus which presents a test optotype to an eye to be examined for testing or measuring visual acuity or the like. More particularly,. the present invention relates to a night visual acuity (night vision) testing apparatus used for a driving aptitude test or the like.

2. Description of Related Art

Conventionally known as a visual acuity testing apparatus is an apparatus which presents test optotypes disposed inside a casing through binocular test windows for testing or measuring visual function such as visual acuity and the like. As this kind of apparatus, there is an apparatus whose optotype presentation optical system is disposed inside a casing in a manner that a test distance of the optotype is optically long distance (for example five meters). The visual acuity test is measured through examining how well an examinee sees the optotypes. Additionally, among this kind of apparatus, there is a night visual acuity testing apparatus which is used for the driving aptitude test or the like. In a night visual acuity testing apparatus, first, the eye is shown space inside the casing that has been adjusted to be as bright as the daytime through the test windows in order to cause light adaptation in the eyes. After this, the optotypes are presented under dark conditions in the space inside the casing, then the visual acuity recovering time is taken until the eye visually identifies the optotypes, which is measured.

However, in a conventional visual acuity testing apparatus, there is a problem such that the shapes of the optotypes are visible because incident light from the test windows enters inside the casing and reflects from surfaces of the optotypes. This causes a problem that a test with high accuracy is hard to be achieved. The problem is much more serious in the night visual acuity testing apparatus. For prevention, conventionally, when the test is carried out in a bright room, for example, the examinee's head is covered with a blackout curtain, which is inconvenient.

Conventional visual acuity testing apparatus adopts a way in which an examinee looks into one casing with the both eyes through the binocular test windows. In case that the both eyes individually look into the casing, the eyes feel uncomfortable upon observing the optotype owing to different distances from a right interior wall and from a left interior wall. Under such observation, it is difficult to produce the conditions that the examinee sees five meters ahead so that accuracy of the test decreases compared with a visual acuity test carried out in real conditions that the examinee sees five meters ahead.

Furthermore, conventional night visual acuity testing apparatus has following problems. In the night visual acuity test, after light adaptation, if the examinee can judge presented optotypes in a visual field (the casing) in the same low brightness, he makes responses with a response switch. The apparatus carries out measurement of the time from start of presenting the optotypes. At a point of inputting results with the response switch, the apparatus stops time measurement. In case that judgement results of the optotypes by the examinee is right, the lapsed time to a point of time when the response is inputted, is determined as the visual acuity recovering time. Additionally, in case that no response is made after 60 seconds from start of measuring the visual acuity recovering time (start of presenting the optotypes), the test is terminated leading the lowest evaluation value as the result. However, if just one response leads the test result as mentioned above, in case that judgement results of optotypes are in error, it is necessary to carry out the test again from the start, which takes time to obtain test results. There is a problem concerning test accuracy considering possibility that a response as the result of a guess happened to be a right response. In the test for the elderly, in many cases, they can not respond after 60 seconds have passed from starting of measurement, thus, the visual acuity recovering time is difficult to be evaluated.

SUMMARY OF THE INVENTION

The present invention has been made in view of the above circumstances and has an object to overcome the above problem and to provide a visual acuity testing apparatus which achieves tests with high accuracy even in a bright room. Additionally, it is also an object of the present invention to provide a visual acuity testing apparatus which produces far-vision without causing uncomfortablness in order to carry out tests with high accuracy.

Further, another object of the present invention is to provide a night visual acuity testing apparatus which can obtain test results with high efficiency and high accuracy, and further more to provide a visual acuity testing apparatus which gives useful test results for evaluating the visual acuity recovering time.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed our in the appended claims.

To achieve the objects and in accordance with the purpose of the invention, as embodied and broadly described herein, a visual acuity testing apparatus comprises a casing having at least one test windows which an examinee looks into and at least one optotype presented inside the casing which is disposed in such a position that its optotype plane is tilted relative to a datum plane orthogonal to an axial line connecting the test window to an optotype presentation position in order to prevent that light entered through the test window and reflected from the optotype plane, passes through the test window again. In another aspect of the present invention, a visual acuity testing apparatus comprises two casings for a right eye and for a left eye having a test window and an optotype presentation window respectively and also having approximately equal distances from the center axis of the test windows to a right wall and to a left wall respectively, optotypes including the same set of optotypes which can be disposed in each of optotype presentation windows simultaneously, inside illuminating means which illuminates the inside of each of the two casings respectively, optotype illuminating means which illuminates each of optotypes disposed in each of optotype presentation windows respectively, test eye designating means which for designating an eye to be examined among a single right eye, a single left eye, and the both, and illumination controlling means which controls the inside illuminating means and the optotype illuminating means separately based on designation by of the test eye designating means. Further, in another aspect of the present invention, a visual acuity testing apparatus comprises mode instructing means which for giving instructions a night visual acuity test for measuring visual acuity recovering time, optotype presentation means which presents at least one test optotype, response means for making a response of a judgement result on the presented optotype, measuring means which measures lapsed time from start of presenting optotype to the response in order to measure the visual acuity recovering time based on the instructions given by the mode instructing means, judging means which judges whether the response agrees with the presented optotype, and determining means which determines a test result based on the number of consecutive right responses or the number of consecutive wrong responses. Furthermore, in another aspect of the present invention, a visual acuity testing apparatus comprises mode instructing means for giving instructions to perform a night visual acuity test for measuring visual acuity recovering time, measuring means which measures lapsed time from start of presenting optotype in order to measure the visual acuity recovering time based on the instructions given by the mode instructing means, optotype presentation means which presents at least one optotype, optotype illuminating means which illuminates the presented optotype, response means for making a response of a judgement result on the presented optotype, and illumination controlling means which changes the amount of illumination light volume by controlling the optotype illuminating means based on presence or absence of the response and the lapse time measured by the measuring means.

BRIEF DESCRIPTION OF THE DRAWINGS

The accompanying drawings, which are incorporated in and constitute a part of this specification illustrated and embodiment of the invention and, together with the description, serve to explain the objects, advantages and principles of the invention. In the drawings.

DETAILED DESCRIPTION OF THE PREFERRED EMBODIMENTS

A detailed description of one preferred embodiment of a visual acuity testing apparatus embodying the present invention will now be given referring to the accompanying drawings.

Figure 1:
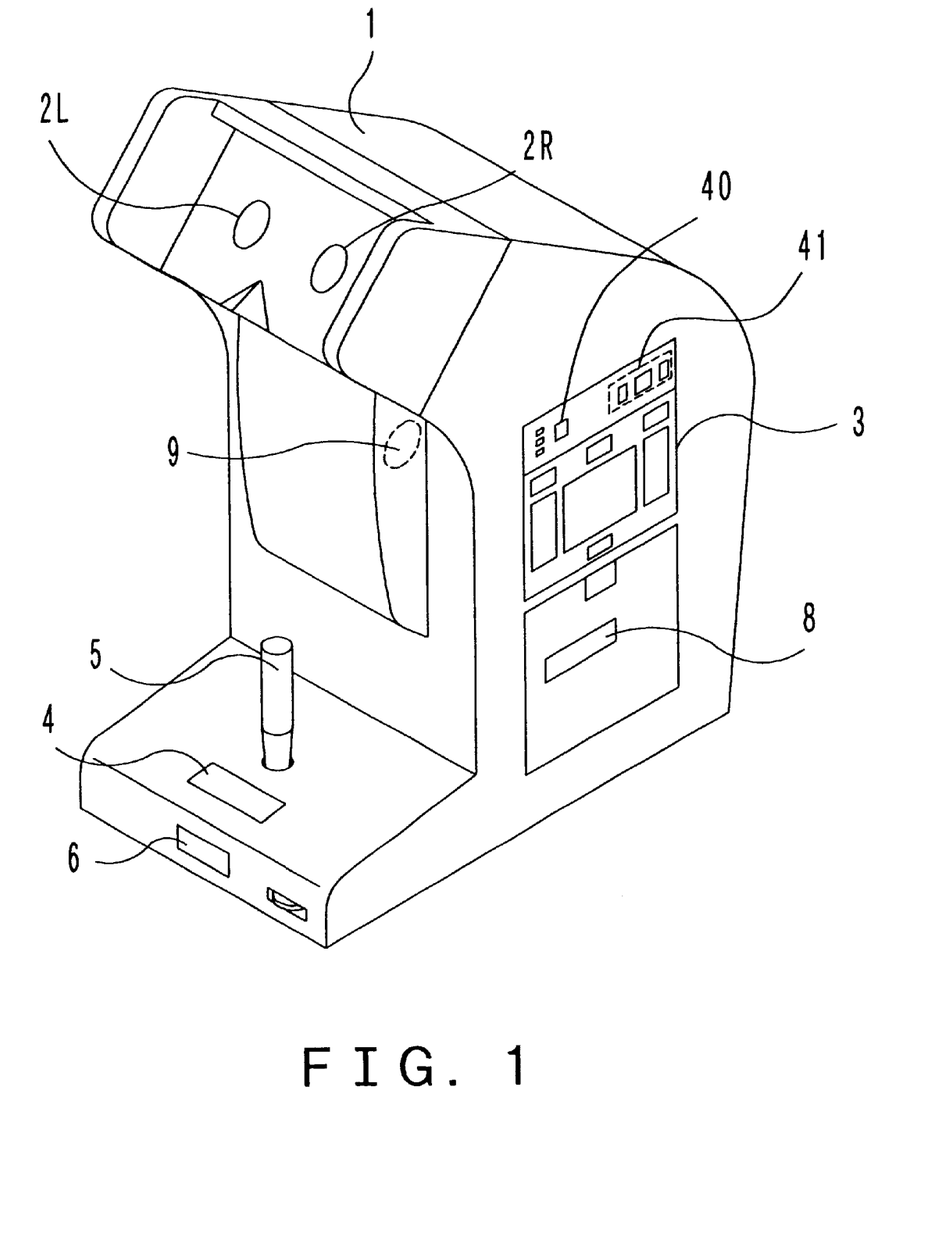
FIG. 1 is a view showing an external representation of a visual acuity testing apparatus of an embodiment consistent with the present invention.

FIG. 1 is a view showing an external representation of a visual acuity testing apparatus of the embodiment consistent with the present invention. In the present embodiment, a night visual acuity (night vision) testing apparatus is explained as one example.

Reference numeral 1 is a main body of the apparatus. Binocular test windows (sight windows) 2 (2R and 2L) for which the examinee looks into presented optotypes therein are provided at the upper part of the main body 1. An operation panel 3 having various switches and a printer 8 are provided on the side of the main body 1. In the lower front of the main body 1, a joystick (lever) 5 with which the examinee responds the orientations of gaps shown by presented optotypes and a response button 4 used when an examinee can not judge optotypes or the like are provided. A start switch 6 is for an auto-testing mode. A speaker 9 outputs a voice-guide.

Figure 2:
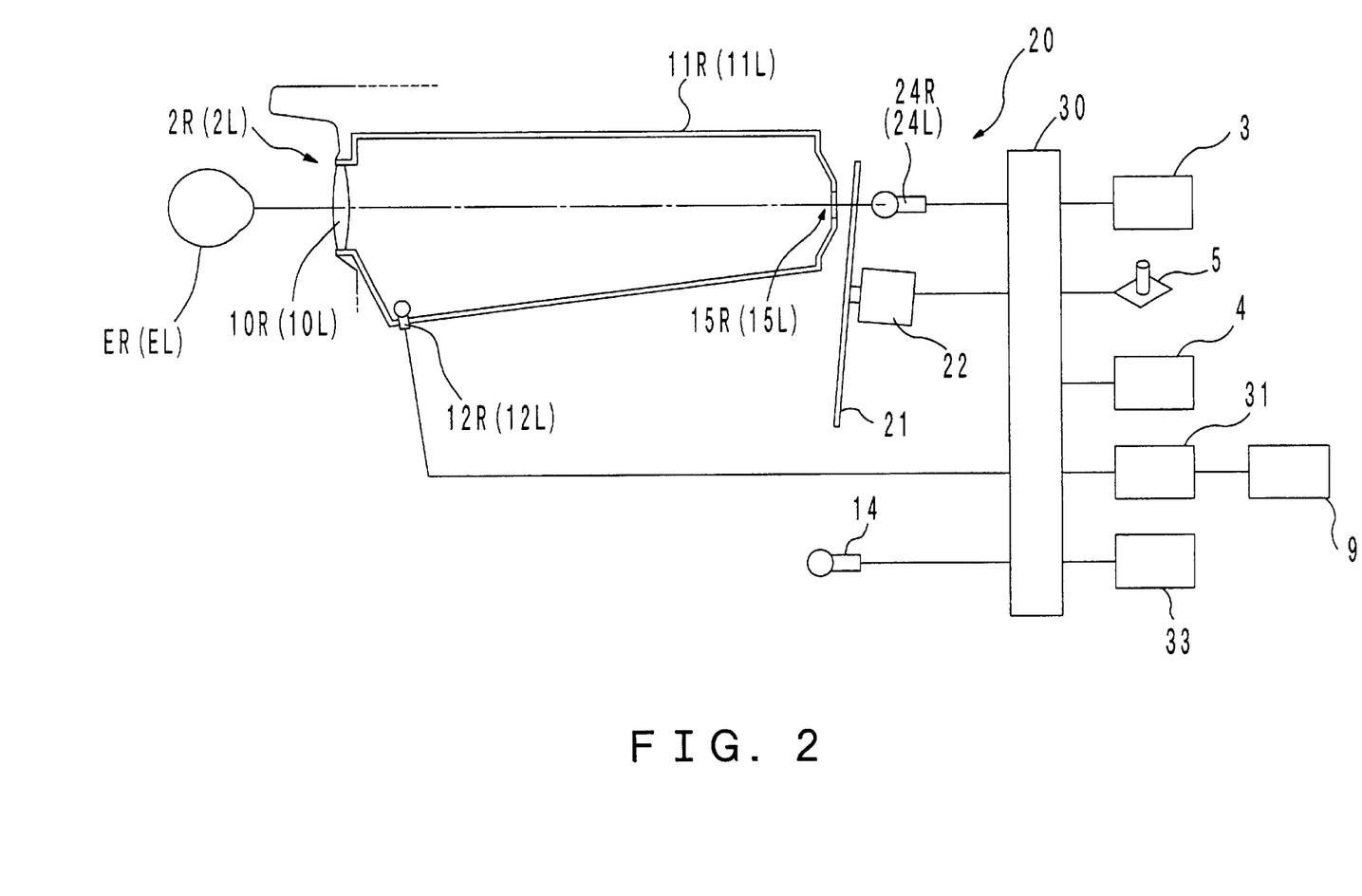
FIG. 2 is a side view showing schematic configurations of an optical system as well as schematic configuration of a control system of the present invention.
Figure 3:
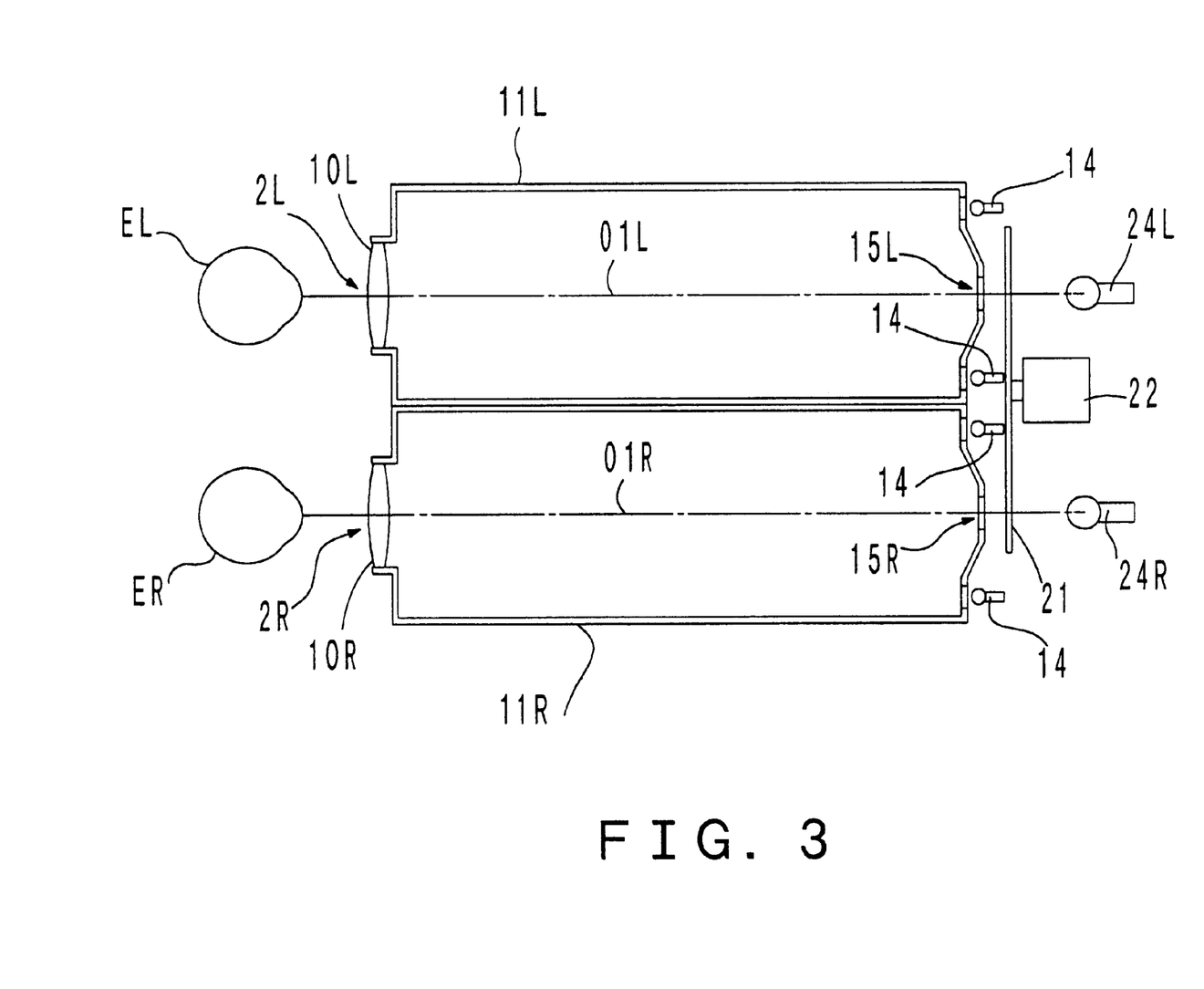
FIG. 3 is a top view showing schematic configurations of the optical system of the present invention.

FIG. 2 is a side view showing schematic configuration of optical system and is also a view showing schematic configuration of a control system. FIG. 3 is a top view showing schematic configuration of the optical system of the present invention.

Lenses 10R and 10L are disposed in the right and left test windows 2R and 2L respectively. Each of the optotypes placed in optotype windows (presentation windows) 15R and 15L appears at a testing distance of five meters from a right eye ER and a left eye EL to be examined. Tube-shaped inside covers 11R and 11L separate right and left paths to ensure visual field space in which optotypes are observed by the eyes ER and EL. The covers 11R and 11L have the same shape and of which right and left inside walls are formed symmetrically about each of center axis lines 01R and 01L of the test windows 2R and 2L (each optical axis of lenses 10R and 10L) (the distance of right and left walls from the center axis lines 01R and 01L are equal). Additionally, the optotype windows 15R and 15L are placed in the same positions (on the central axis lines 01R and 01L). Accordingly, when observing the insides of inside covers 11R and 11L through the test windows 2R and 2L with the both eyes, the only one optotype window can be observed in a like manner when observing the optotype window with a single eye (either of the both eyes) (when looking inside with the both eyes, two optotype windows 15R and 15L appear to be fused). Together with this, the insides of the inside covers 11R and 11L (visual field space) also appear to be one space. For this reason, the examinee can observe optotypes placed in an optical long distance (five meters) without uncomfortableness.

Further, the inside walls of the inside covers 11R and 11L are painted matte white. When carrying out an ordinal visual acuity test or light adaptation for measuring a visual acuity recovering time, the insides of the inside covers 11R and 11L are maintained predetermined brightness by turning on illumination lamps 12R and 12L. The illumination lamps 12R and 12L are disposed in a position which their illumination light does not make incident directly on the eyes ER and EL.

Furthermore, illumination lamps 14 light up when performing a visual acuity test under dazzling, which has the same brightness as vehicular headlights are disposed in right and left sides of each of the optotype windows 15R and 15L. The visual acuity test under dazzling is performed by lighting up the illumination lamps 14 for testing the influence of dazzling cased by headlights of oncoming vehicles and the like when driving at night.

An optotype presentation unit 20 places optotypes in each of the optotype windows 15R and 15L. The presentation optotype unit 20 is provided with one optotype disk 21, a pulse motor 22 for driving the optotype disk 21, and a pair of illumination lamps 24R and 24L for illuminating optotypes on the optotype disk 21.

The optotype disk 21 is comprised of a translucent glass board. On the glass board, Landolt rings in 12 different patterns corresponding to visual acuity value of 0.1–1.0, 1.2, 1.5 and with gaps in one of four orientations: up, down right and left are formed by chrome coating having shading characteristic. Those optotypes are formed corresponding to positional relationships of a pair of the optotype windows 15R and 15L in a manner that a pair of the same set of optotypes for presentation for a right eye and for a left eye can be presented to the eyes ER and EL at the same time. Moreover, on the optotype disk 21, besides Landolt rings, a shield board is equipped for shielding the optotype windows 15R and 15L at light adaptation of a night visual acuity test. Instead of forming on a sheet of optotype disk, optotypes for presentation for a right eye and for a left eye may be formed on two sheets of optotype disks.

As for optotypes on the optotype disk 21, rotation of the motor 22 places a pair of the same optotypes in the optotype windows 15R and 15L. Then, the illumination lamps 24R and 24L illuminate each of the optotypes. At an ordinal visual acuity test, optotypes are presented in about 250 $cd/m^2$ brightness by lightning up the illumination lamps 24R and 24L. Additionally, when measuring the visual acuity recovering time, the amount of light volume of the illumination lamps 24R and 24L is decreased, so that optotypes are usually presented in low brightness such as 0.15 $cd/m^2$.

As mentioned above, in case of a test in which illumination brightness is turned down, in case that incident light from the binocular test windows 2 is reflected from the optotype plane and reaches to the eyes ER and EL. Because of this, the examinee observes optotypes undesirably so that a test with high accuracy is difficult to be performed. For solving this problem, as showed in FIG. 4, an optotype plane of the optotype disk 21 is tilted to make an angle of θ degrees relative to a plane M orthogonal to the center axis line 01 (an axis line which connects the center of the test windows 2 to an optotype presentation position P) so as to prevent light reflected from the optotype plane from reaching the eyes ER and EL. This tilt angle θ is determined in following steps.

Figure 4:
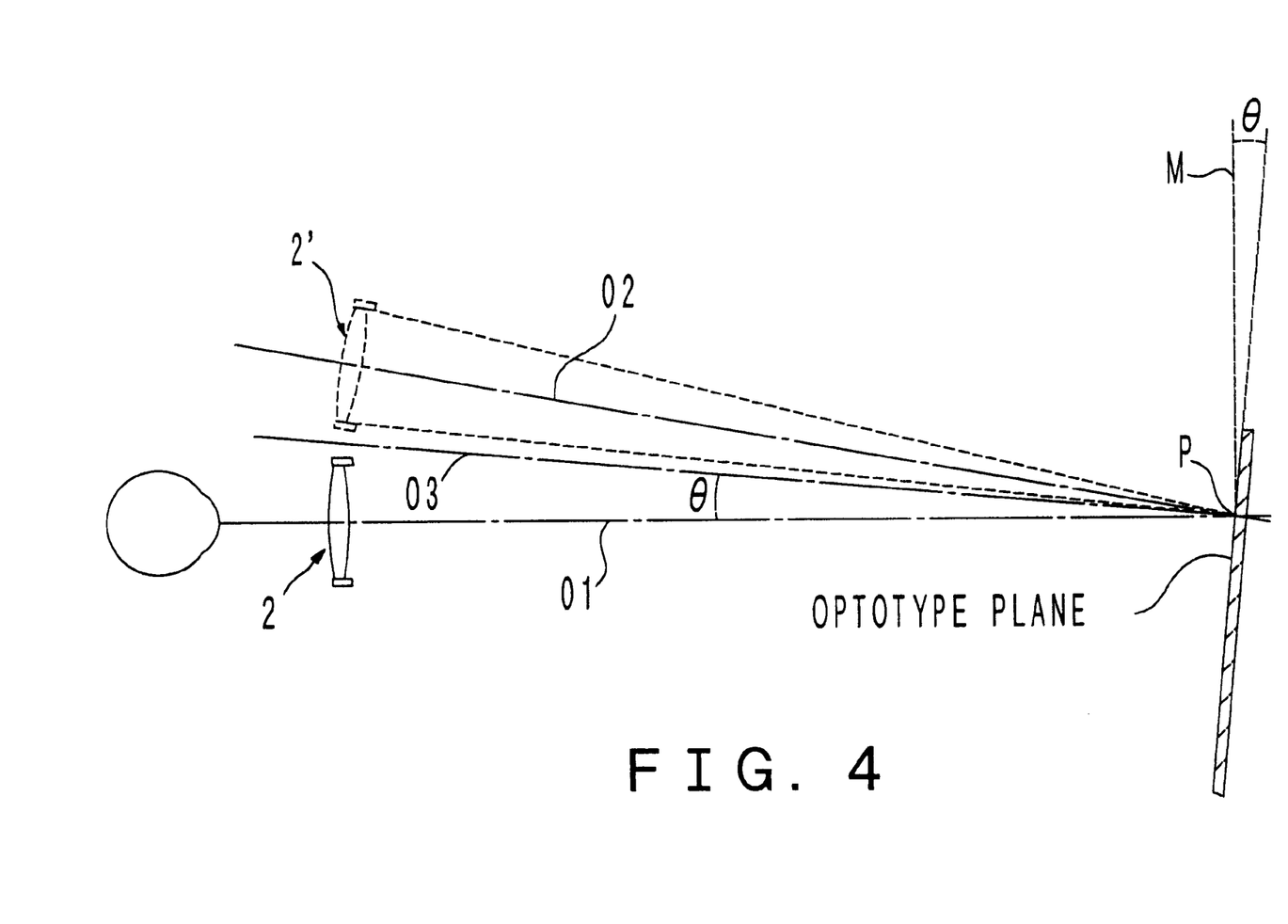
FIG. 4 is a view illustrating how to determine a tilt angle of an optotype plane.

First, as showed in FIG. 4, imagine a position in which the test windows 2 and imaginary windows 2' having the same diameter as the test windows 2, are not overlapped. Next, generates a center axis line 02, which connects the center of the imaginary windows 2' to the optotype presentation position P. Then, set a center axis line 03, which is positioned at a midpoint of the angle formed between the center axis line 02 and the center axis line 01 at the optotype presentation position P. Further, dispose the optotype plane in a position orthogonal to the center axial line 03 at the optotype presentation position P. This prevents incident light from the test windows 2, which is reflected from the optotype plane by passing through the test windows 2 again. As a result of this, the light reflected from the optotype plane is invisible even if the examinee looks into the casing from any positions of the test windows 2.

For instance, in case that the diameter of the test windows 2 is 24 mm and the real distance from the test windows 2 to the optotype presentation position P is 240 mm, according to an expression $\theta = \tan^{-1}(12/240)$, angle is about 2.9 degrees. Accordingly, the optotype plane may be tilted over three degrees.

In the present embodiment, configurations are such that optical path for which the eye ER and EL observes optotypes, is separated. In an apparatus in which optotypes are disposed in the center of one casing, the above-mentioned tilt of optotypes can be applied in the same manner.

In FIG. 2, a control unit 30 controls the all parts of the apparatus and is connected to each of the lamps, the pulse mortar 22, a voice-guide generating unit 31 connected to the speaker 9, the response button 4, the joystick 5, the operation panel 3, a memory 33 storing the test program and the like.

Next, operation of the apparatus having the above-mentioned configurations is explained. The present apparatus is provided with three test modes: a manual mode, an auto mode (in which the test is carried out in accordance with the program by examinee's switch operations following the voice-guide and a semi-auto mode (in which test is carried out in accordance with the program by examiner's switch operations consistent with examinee's oral responses). Any of the modes can be selected with a mode-selecting switch 40 of the operation panel 3. A test carried out in the auto mode is explained as follows. The auto mode is programmed in a manner that an ordinal visual acuity test (a visual acuity test at a five-meters-distance), measurement of the visual acuity recovering time (a night visual acuity test) and a visual acuity test under dazzling are carried out in turn. Eyes to be examined are predetermined with a switch unit 41. The eye can be selected among a single right eye, a single left eye and the both eyes. In this time, the both eyes are selected.

The examinee pushes the start switch 6, which starts to perform an ordinal visual acuity test first. The control unit 30 turns on the illumination lamps 12R and 12L to brighten the insides of the inside covers 11R and 11L to maintain 30 $cd/m^2$ brightness. The control unit 30 also controls drive of the pulse motor 22 and the illumination lamps 24R and 24L lightning up, and then presents the same set of optotypes corresponding to visual acuity value of 0.5 to the optotype windows 15R and 15L respectively. After judging a direction of optotypes (orientations of gaps of Landolt ring) with the voice-guide, the examinee follows instructions of the voice-guide, which makes the examinee tilt the joystick 5 in a direction of the judgement result. The examiner responds a judgement result of an optotype with the joystick 5. The control unit 30 judges whether the response is right or wrong. If the response is correct, an optotype whose visual acuity value is one level higher than the previous one is presented. On the other hand, if the response is wrong, an optotype whose visual acuity is one level lower than the previous one is presented. In case that the examinee can not judge the optotype whose visual acuity value is one level higher than the previous one, or in case that he responds wrong (when the examinee can not judge the optotype, he pushes the response button 4), visual acuity value of optotypes is set once again for the previous optotype, and the test is continued to be performed with the visual acuity value of optotypes having different directions. The control 30 judges that the examinee identifies that visual acuity value when more than two consecutive right responses are made with the same visual value of optotypes.

Figure 5:
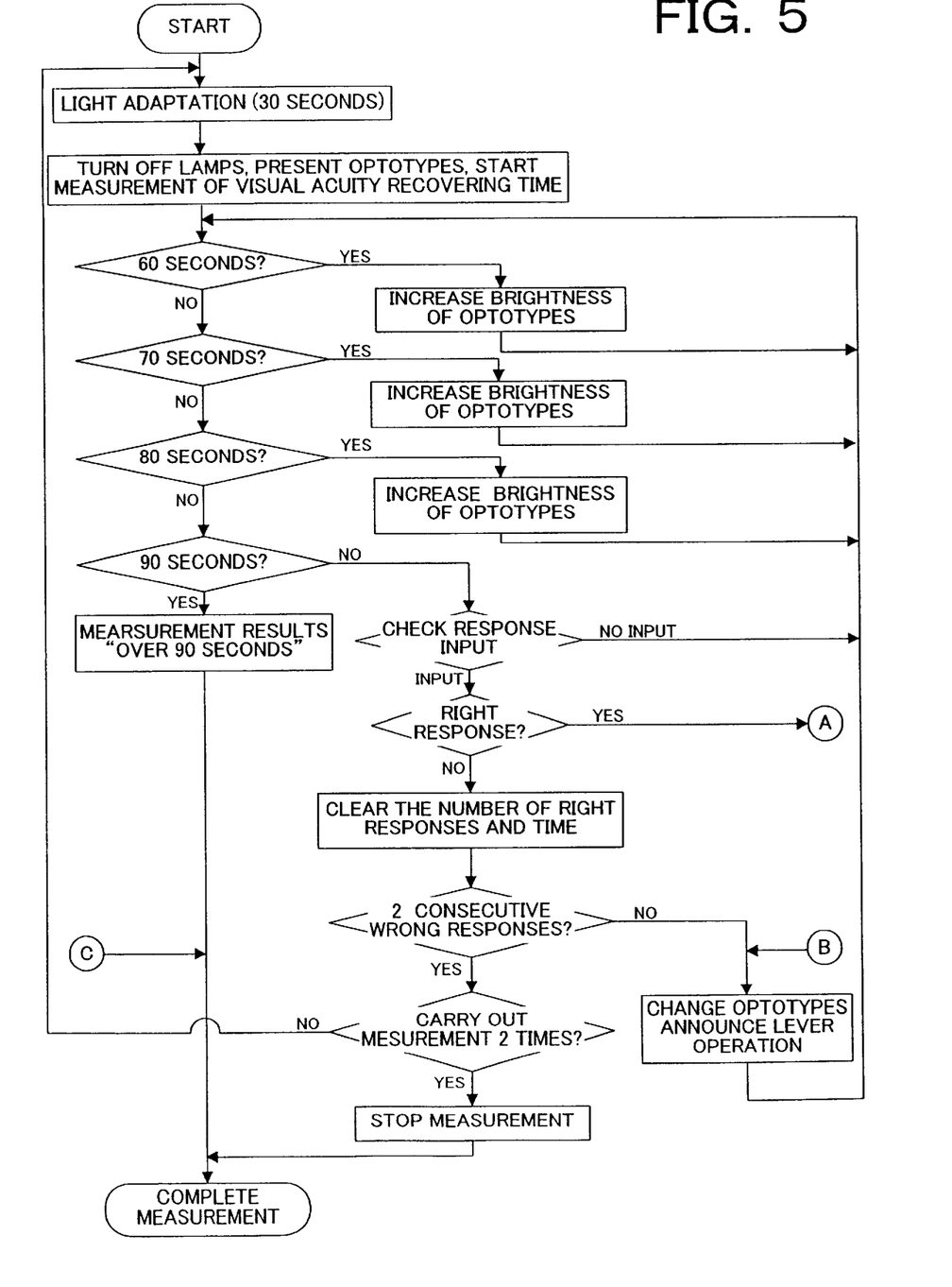
FIG. 5 is a flow chart illustrating measurement of the visual acuity recovering time.
Figure 6:
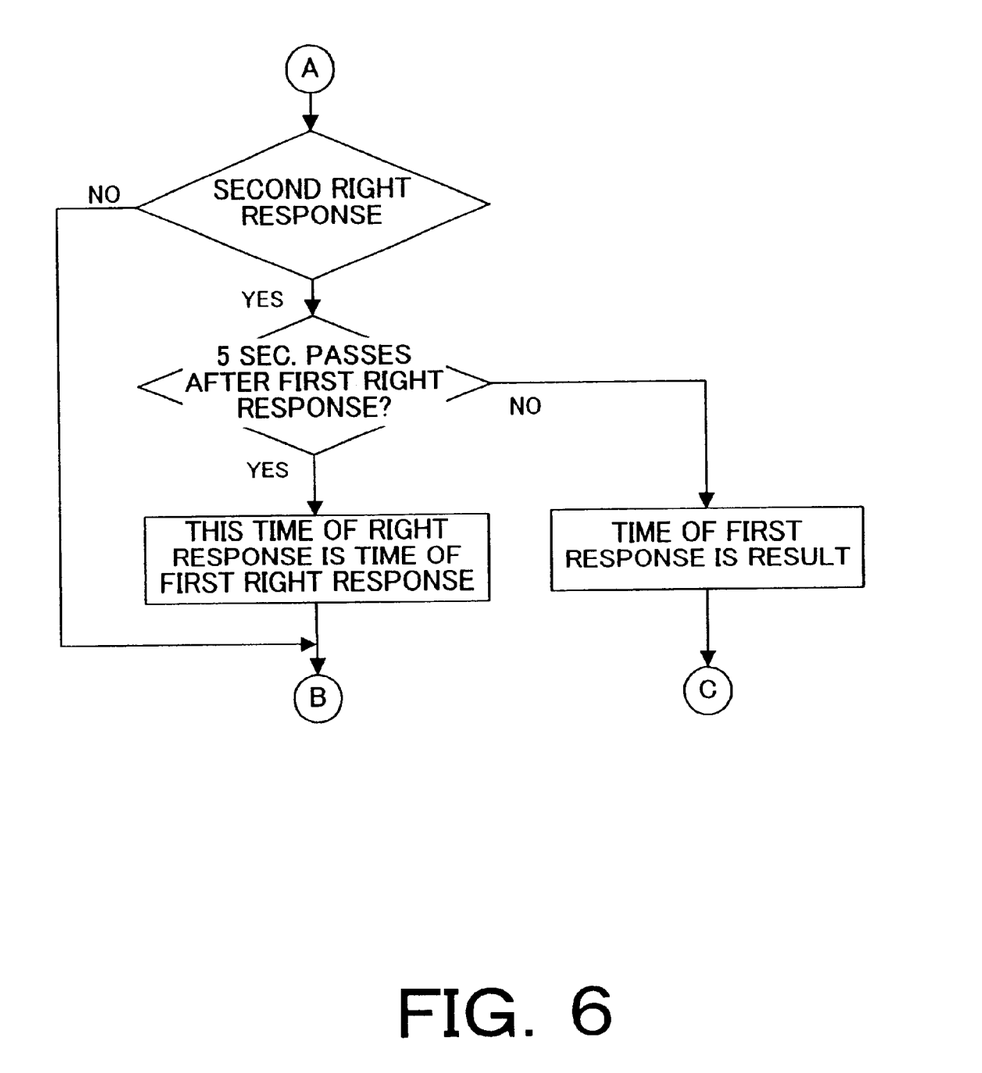
FIG. 6 is a flow chart illustrating measurement of the visual acuity recovering time.

Next, a program of measurement of the visual acuity recovering time is performed (See flow charts in FIGS. 5 and 6). The voice-guide announces that the illumination lamps 12R and 12L light up for 30 seconds. After this, the control unit 30 illuminates the insides of the inside covers 11R and 11L (visual field space) with the illumination lamps 12R and 12L, and starts measuring time at which the eyes ER and EL adapt light. During this, the shield board furnished with the optotype disk 2 is disposed in the optotype windows 15R and 15L.

At nearly-completed time of light adaptation, the voice-guide says, "After turning off the lights, tilt the lever in an orientation of gap as soon as you can recognize an optotype." After turning off of light adaptation, the same set of optotypes corresponding to 0.2 visual acuity value are disposed in the optotype windows 15R and 15L as soon as the illumination lamps 12R and 12L are turned off. Each of optotypes is presented in low brightness such as 0.15 $cd/m^2$ with the illumination lamps 24R and 24L. The control unit 30 measures the time from the start of presenting optotypes and checks judgement results of response inputted with the joystick 5. In case that no response is made after 60 seconds (or in case that a response is wrong), the optotype brightness is set up twice as high as the optotype brightness on start (about 0.30 cd/m$^2$). Further, in case that no response is made after 70 seconds, the optotype brightness is set up three times as high as the optotype brightness on start (0.45 cd/m$^2$). Furthermore, in case that no response is made after 80 seconds, the optotype brightness is set up four times as high as the optotype brightness on start (0.60 cd/m$^2$). As mentioned above, after 60 seconds have passed, the time at which the test is completed, is extended, and optotype brightness is also set up gradually every 10 seconds. With this procedure, it raises a possibility that even the examinee who can not make a response in the optotype brightness on start, he can make visual identification. After 90 seconds, the test is completed and determined a test result as "90 seconds lapses".

After a response is inputted with the joystick 5, the control unit 30 judges whether the response is right or wrong. In the case in which the response is wrong and yet is the first wrong response (two consecutive wrong responses are not made), a direction of presented optotypes is changed. Further, the voice-guide saying that "Please tilt the lever in a direction of a gap of the ring" is announced, and the test goes on (when the response is wrong, it is not dealt with as the test result because the examinee has not made visual recognition of an optotype with reliability). Moreover, in case that next response is inputted and is also wrong (consecutive two wrong answers are made), the test is automatically performed again from light adaptation. Additionally, the test can be performed again only once. In case that the test is performed again, and yet, consecutive wrong responses are made twice, the test is stopped and measurement of the visual acuity recovering time itself is terminated.

In case that a response is judged right and is the first response(two consecutive right responses are not made), after a direction of the presented optotype is changed in the same manner as mentioned above, the voice-guide saying that "Please tilt the lever in a direction of a gap of the ring" is announced. Then, when next response is correct and made within 5 seconds after the previous right response, it is judged that the two consecutive right responses are made. In this case, the examinee has managed to make visual recognition so that the measurement time of the first response in consecutive responses is determined as the test result (the visual acuity recovering time). If the second response is made over five seconds later from the previous right response, the previous response is judged less reliable (that is, at the previous response, if the examiner has surely made visual acuity recognition, he should be able to make recognize the next presented optotype quickly). For this reason, the responses are not judged as two consecutive right responses and the previous response is also treated as wrong. The time of right responses in this time is determined as the time of the first right response.

As mentioned above, in case that two consecutive right responses are made, the time of the first response in the consecutive responses is determined as the visual acuity recovering time. This can increase credibility of the test result. In case of one wrong response (two consecutive wrong responses are not made), tests do not have to be performed again unnecessary so that the test continue to be formed.

After completing the measurement of the visual acuity recovering time, next, a visual acuity test under dazzling is performed. The voice-guide instructs the examinee to observe an optotype carefully and respond its direction of a gap. Then, the control unit 30 turns on the illumination lamps 14 disposed in the both sides of the optotype windows 15R and 15L. The same set of optotypes corresponding to visual acuity value of 0.5 (or the optotype corresponding to visual acuity value which is determined in an ordinal visual acuity test finally) is presented to the optotype windows 15R and 15L. The control unit 30 judges whether the responses are right or wrong in the same manner as an ordinal visual acuity test. As a result of this, an optotype to be presented next is determined. If more than two right responses are made with optotypes having the same visual acuity value, it is judged that the examinee identifies that visual acuity value.

After all tests are completed, the printer 8 automatically prints out each of test results, judgement results of each test, comprehensive guidance and so on.

The visual acuity test for the both eyes has been explained as mentioned above. For instance, in case that the visual acuity test only for a right eye is designated with the switch unit 41, the control unit 30 turns on the designated side of the illumination lamps (12R, 15R and 14) as described above and the lamps for a left eye is kept of f. As such, the lamps disposed are controlled their on-and-off states, which allows the test. eyes switching. For this reason, a conventional switching right and left eye mechanism with the shield board (a mechanism which test eyes are switched by inserting the shield board in front of the eyes) does not have to be equipped so that the apparatus can be of low cost.

As explained above, according to the present invention, highly accurate test can be achieved by producing a far-vision state without causing uncomfortableness even in a bright room.

Additionally, in the night visual acuity test, test results with high credibility can be obtained efficiently. The useful test results for evaluating the visual acuity recovering time also can be gained.

The foregoing description of the preferred embodiment of the invention has been presented for purposes of illustration and description. It is not intended to be exhaustive or to limit the invention to precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto and their equivalents.

What is claimed is:

1. A visual acuity testing apparatus comprising: a casing having at least one test window which an examinee looks into; and at least one optotype presented inside the casing which is disposed in such a position that its optotype plane is tilted relative to a datum plane orthogonal to an axial line connecting the test window to an optotype presentation position in order to prevent that light entered through the test window and reflected from the optotype plane, passes through the test window again.

2. The visual acuity testing apparatus according to claim 1, wherein the tilt angle at which the optotype plane of the optotype forms with the datum plane is greater than an angle θ given by the following expression:

θ=tan$^{-1}$ (radius of the test window/distance from the test window to the optotype presentation position).

3. The visual acuity testing apparatus according to claim 1, wherein the casing is provided with two casings for a right eye and for a left eye, each of the two casings has the test window and an optotype presentation window respectively, and the optotype includes the same set of optotypes which can be disposed in each of the optotype presentation windows simultaneously, and the apparatus further comprising:

inside illuminating means which illuminates the inside of each of the two casings respectively;

optotype illuminating means which illuminates each of the optotypes disposed in each of the optotype presentation windows respectively;

test eye designating means for designating an eye to be examined from a single right eye, a single left eye or the both; and illumination controlling means which controls the inside illuminating means and the optotype illuminating means separately based on the designation by the test eye designating means.

4. The visual acuity testing apparatus according to claim 3, wherein each of the two casings has approximately equal distances from the center axis of each of the test windows to a right inner wall and to a left inner wall respectively.

5. The visual acuity testing apparatus according to claim 1, further comprising:

mode instructing means for giving instructions to perform a night visual acuity test for measuring visual acuity recovering time;

inside illuminating means which illuminates the inside of the casing;

optotype illuminating means which illuminates the presented optotype; and illumination controlling means which controls the inside illuminating means and the optotype illuminating means separately based on the instructions given by the mode instructing means.

6. The visual acuity apparatus according to claim 1, further comprising:

mode instructing means for giving instructions to perform a night visual acuity test for measuring visual acuity recovering time;

response means for making a response of a judgement result on the presented optotype;

measuring means which measures lapsed time from start of presenting optotype to the response in order to measure the visual acuity recovering time based on the instructions given by the mode instructing means;

judging means which judges whether the response agrees with the presented optotype; and determining means which determines a test result based on the number of consecutive right responses or the number of consecutive wrong responses.

7. The visual acuity testing apparatus according to claim 1, further comprising:

mode instructing means for giving instructions to perform a night visual acuity test for measuring visual acuity recovering time;

measuring means which measures lapsed time from start of presenting optotype in order to measure the visual acuity recovering time based on the instructions given by the mode instruction means;

optotype illuminating means which illuminates the presented optotype;

response means for making a response of a judgement result on the presented optotype; and illumination controlling means which changes the amount of illumination light volume by controlling the optotype illuminating means based on whether presence or absence of the response and the lapsed time measured by the measuring means.

8. A visual acuity testing apparatus comprising:

two casings for a right eye and for a left eye having a test window and an optotype presentation window respectively, and also having approximately equal distances from the center axis of each of the test windows to a right inner wall to a left inner wall respectively;

optotypes including the same set of optotypes which can be disposed in each of optotype presentation windows simultaneously;

inside illuminating means which illuminates the inside of each of the two casings respectively;

optotype illuminating means which illuminates each of optotypes disposed in each of the optotype presentation windows respectively;

test eye designating means for designating an eye to be examined among a single right eye, a single left eye, and the both; and illumination controlling means which controls the inside illuminating means and the optotype illuminating means separately based on designation by the test eye designating means.

9. The visual acuity testing apparatus according to claim 8 further comprising:

mode instructing means for giving instructions to perform a night visual acuity test for measuring visual acuity recovering time, and wherein the illumination controlling means controls the inside illuminating means and optotype illuminating means separately based on designation by the test eye designating means and the instructions given by mode instruction means.

10. A visual acuity testing apparatus comprising:

mode instructing means for giving instructions to perform a night visual acuity test for measuring visual acuity recovering time;

optotype presentation means which presents at least one test optotype;

response means for making a response of a judgement result on the presented optotype; and measuring means which measures lapsed time from start of presenting optotype to the response in order to measure the visual acuity recovering time based on the instructions given by the mode instructing means;

judging means which judges whether the response agrees with the presented optotype; and determining means which determines a test result based on the number of consecutive right responses or the number of consecutive wrong responses.

11. The visual acuity testing apparatus according to claim 10, wherein the determining means determines the lapsed time up to when the first right response of the consecutive right responses is made as the visual acuity recovering time in case that at least two consecutive right responses are made.

12. The visual acuity testing apparatus according to claim 10, wherein the determining means determines that the visual acuity recovering time is not obtained in case that at least two consecutive wrong responses are made.

13. The visual acuity testing apparatus according to claim 10, wherein the measuring means further measures lapsed time from input of the first response to input of the second response which is continuous with the input of the first response, and the determining means determines that the first response is wrong in case that the lapsed time up to the input of the first response to the input of the second response is over a predetermined time even if the judging means judges that the second response is right.

14. A visual acuity testing apparatus comprising:

mode instructing means for giving instructions to perform a night visual acuity test for measuring visual acuity recovering time;

measuring means which measures lapsed time from start of presenting optotype in order to measure the visual acuity recovering time based on the instructions given by the mode instructing means;

optotype presentation means which presents at least one optotype;

optotype illuminating means which illuminates the presented optotype;

response means for making a response of a judgement result on the presented optotype; and illumination controlling means which changes the amount of illumination light volume by controlling the optotype illuminating means based on presence or absence of the response and the lapse time measured by the measuring means.

15. The visual acuity testing apparatus according to claim 14, wherein the illumination controlling means increases the amount of illumination light volume in case that no response is made with the response means when the lapsed time is over the predetermined time.

16. The visual acuity testing apparatus according to claim 14, wherein the illumination controlling means increases the amount of illumination light volume in stages according to the measured lapsed time in case that no response is made with the response means.

17. The visual acuity testing apparatus according to claim 14, further comprising:

judging means which judges whether the response agrees with the presented optotype, and wherein the illumination controlling means controls the optotype illuminating means such that no response is made with the response means in case that the judging means judges the response as wrong.

* * * * *